(12) United States Patent  
Sue et al.

(10) Patent No.: US 9,084,699 B2
(45) Date of Patent: Jul. 21, 2015

(54) ABSORBENT ARTICLE

(75) Inventors: Shunketsu Sue, Mason, OH (US); Ebrahim Rezai, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 732 days.

(21) Appl. No.: 12/707,212

(22) Filed: Feb. 17, 2010

(65) Prior Publication Data

US 2010/0217216 A1    Aug. 26, 2010

Related U.S. Application Data (60) Provisional application No. 61/154,142, filed on Feb. 20, 2009.

(51) Int. Cl.
*A61F 13/15* (2006.01)
*A61F 13/515* (2006.01)
*A61F 13/539* (2006.01)

(52) U.S. Cl.
CPC ......... *A61F 13/515* (2013.01); *A61F 13/15699* (2013.01); *A61F 2013/15406* (2013.01); *A61F 2013/15569* (2013.01); *A61F 2013/53908* (2013.01)

(58) Field of Classification Search
CPC ............... A61F 13/515; A61F 13/539; A61F 2013/15284; A61F 2013/15406; A61F 2013/15569; A61F 2013/53908; A61F 2013/53916; A61F 2013/53925; A61F 2013/53933; A61F 2013/53941
USPC .......................................... 604/365, 372, 378
See application file for complete search history.

(56) References Cited

U.S. PATENT DOCUMENTS

| 3,239,478 A | 3/1966 | Harlan, Jr. |
| 3,427,269 A | 2/1969 | Davis et al. |
| 3,700,633 A | 10/1972 | Wald et al. |
| 3,753,936 A | 8/1973 | Marrs |
| 3,860,003 A | 1/1975 | Buell |
| 3,932,327 A | 1/1976 | Naylor |
| 4,610,678 A | 9/1986 | Weisman et al. |
| 4,673,402 A | 6/1987 | Weisman et al. |
| 4,808,178 A | 2/1989 | Aziz et al. |
| 4,834,735 A | 5/1989 | Alemany et al. |
| 4,888,231 A | 12/1989 | Angstadt |
| 4,909,803 A | 3/1990 | Aziz et al. |
| 5,137,537 A | 8/1992 | Herron et al. |
| 5,147,345 A | 9/1992 | Young et al. |

(Continued)

FOREIGN PATENT DOCUMENTS

JP        11-239587        9/1999

OTHER PUBLICATIONS

PCT International Search Report, PCT/US2010/024542 dated Feb. 18, 2010.

(Continued)

*Primary Examiner* — Lynne Anderson
(74) *Attorney, Agent, or Firm* — Kathleen Y. Carter; John G. Powell (57) ABSTRACT

A disposable absorbent article that includes a first and second substrate, a portion of which is joined together with a hot-melt adhesive applied at a temperature of less than 130° C. At least one of the first second substrates has a basis weight of less than 15 grams per square meter. The adhesive provides suitable bond strength on low basis weight substrates and allows for flexible processing conditions.

19 Claims, 8 Drawing Sheets

(56) References Cited

U.S. PATENT DOCUMENTS

| | | | |
|---|---|---|---|
| 5,151,092 | A | 9/1992 | Buell et al. |
| 5,221,274 | A | 6/1993 | Buell et al. |
| 5,260,345 | A | 11/1993 | DesMarais et al. |
| 5,342,338 | A | 8/1994 | Roe |
| 5,387,207 | A | 2/1995 | Dyer et al. |
| 5,397,316 | A | 3/1995 | LaVon et al. |
| 5,554,145 | A | 9/1996 | Roe et al. |
| 5,569,234 | A | 10/1996 | Buell et al. |
| 5,580,411 | A | 12/1996 | Nease et al. |
| 5,625,222 | A | 4/1997 | Yoneda et al. |
| 6,004,306 | A | 12/1999 | Robles et al. |
| 6,380,292 | B1 | 4/2002 | Gibes et al. |
| 6,533,765 | B1 * | 3/2003 | Blaney et al. ............ 604/385.26 |
| 7,013,941 | B2 | 3/2006 | Schneider et al. |
| 7,683,114 | B2 | 3/2010 | Paul et al. |
| 7,838,590 | B2 * | 11/2010 | Kanderski ..................... 524/578 |
| 2003/0022584 | A1 * | 1/2003 | Latimer et al. ................ 442/414 |
| 2004/0122398 | A1 * | 6/2004 | Schnabel et al. ......... 604/385.01 |
| 2004/0162536 | A1 | 8/2004 | Uwe et al. |
| 2004/0167486 | A1 | 8/2004 | Busam et al. |
| 2005/0095941 | A1 * | 5/2005 | Coronado et al. ............ 442/327 |
| 2006/0155253 | A1 | 7/2006 | Dziezok et al. |
| 2006/0155254 | A1 | 7/2006 | Sanz et al. |
| 2007/0027436 | A1 * | 2/2007 | Nakagawa et al. ........... 604/368 |
| 2007/0055211 | A1 | 3/2007 | Shunketsu et al. |
| 2007/0173153 | A1 * | 7/2007 | Paul et al. ..................... 442/149 |
| 2008/0319408 | A1 | 12/2008 | Uchimoto et al. |
| 2010/0010464 | A1 * | 1/2010 | Nishitani et al. ......... 604/385.01 |
| 2010/0121296 | A1 * | 5/2010 | Noda et al. .................... 604/367 |

OTHER PUBLICATIONS

US 8,293,969, 10/2012, Uchimoto et al. (withdrawn).

* cited by examiner

ABSORBENT ARTICLE

CROSS REFERENCE TO RELATED APPLICATIONS

This application claims the benefit of U.S. Provisional Application No. 61/154,142, filed Feb. 20, 2009.

FIELD OF THE INVENTION

Disclosed is an absorbent article that includes a low application temperature adhesive and a low basis weight substrate and a process for making the absorbent article.

BACKGROUND OF THE INVENTION

Adhesives based on block copolymer rubbers are commonly used in the construction of disposable absorbent articles (e.g., diapers, training pants, feminine hygiene articles, adult incontinence devices, and the like) and are sometimes referred to as construction adhesives or chassis adhesives. Commonly used chassis adhesives include so-called "hot-melt" adhesives (i.e., adhesives that exhibit fluid or fluid-like behavior when exposed to a particular temperature or range of temperatures), which are typically used to join nonwovens and/or films to each other and/or other absorbent article components. Hot-melt adhesives are typically applied to a nonwoven or film substrate at temperatures above 130° C. and often above 150° C. Traditional hot-melt adhesives are well known in the art and generally have a formulation that includes a polymer for providing cohesive strength; a tackifying resin or analogous material for providing adhesive strength; waxes, plasticizers or other materials for modifying viscosity (i.e., flowability); and/or other additives including, but not limited to, antioxidants or other stabilizers, pigments, and/or fillers.

Applying hot-melt adhesives to a substrate at temperatures of 150° C. or more may be unsuitable for some manufacturing processes that utilize substrates susceptible to thermal damage from the hot-melt adhesive. Thermal damage to the substrate may result in aesthetic and/or structural defects in a finished product (e.g., holes, weakened areas, brittle areas, wrinkled or gathered areas, discolored areas, areas of reduced elasticity and/or extensibility, and combinations of these). Therefore, it may be desirable to apply a hot-melt adhesive to a substrate at a temperature of less than 150° C. or even less than 130° C. to potentially reduce the risk of thermal damage to the substrate. Adhesives that are intended to be applied to a substrate at temperatures less than 130° C. or 150° C. are sometimes referred to as low application temperature adhesives. The use of low application temperature adhesives may reduce the likelihood of thermal damage to a substrate, reduce the energy consumption of process equipment, and/or reduce the thermal aging of process equipment. Using low application temperature adhesives may even provide a safer work environment.

Conventional low application temperature hot-melt adhesives typically use lower molecular weight polymers and/or higher levels of diluent (e.g., waxes or oils) to lower the viscosity of the adhesive. The lower viscosity of conventional low application temperature hot-melt adhesives may be relatively non-problematic when applied to conventional substrates. However, some manufacturers have turned to lower basis weight substrates to realize a cost savings in the face of a highly competitive marketplace. Other manufacturers may use low basis weight substrates to provide a particular consumer benefit (e.g., increased softness). When the lower viscosity adhesive is applied to a low basis weight substrate, undesirable "bleed-through" may occur. That is, the adhesive may pass all the way through the substrate from one side to the other. Such adhesive bleed-through has been known to lead to cosmetic defects in the substrate or article and/or undesirable transfer of adhesive to other articles (e.g., clothing, skin, furniture, packaging). Additional plasticizer may also result in lower bond strength between the substrates due to a corresponding lower ratio of polymer and/or tackifier to plasticizer.

In addition to the problems described above, conventional hot-melt adhesives (including low application temperature hot-melt adhesives) may not be suitable for use with conventional process equipment over a desired range of process conditions. Conventional hot-melt adhesives are typically liquefied, for example, using a hot-melt tank and subsequently transported via a pump to the point of application (e.g., the surface of a substrate). Along the way, the adhesive may pass through a variety of other components and/or be subjected to a variety of process conditions and shear rates. Generally, at the point of application, the substantially liquefied adhesive composition will pass through a nozzle, bank of nozzles, or some other mechanical element such as a slot. In some manufacturing processes, it may be desirable or even necessary to vary the manufacturing line speed, depending on, for example, the size or shape of the articles being produced and/or the number of articles to be produced in a particular amount of time. In order to apply a consistent amount of adhesive to each product being produced, the rate at which the adhesive is applied may need to be decreased or increased to correspond to a slower or faster manufacturing line speed. One way to change the rate at which the adhesive is applied may be to change the application pressure of the adhesive and thereby increase the flowrate of adhesive through the applicator nozzle. However, changing the application pressure of the adhesive may change the shear rate to which the adhesive is subjected, and thus change the shear viscosity of the adhesive. For example, it is known that an increase in shear rate (e.g., due to a corresponding increase in the pressure applied to the adhesive in the adhesive applicator) may cause a phenomenon in certain fluids known as shear thinning (i.e., a decrease in shear viscosity). On the other hand, decreasing the shear rate may have the opposite effect (i.e., the fluid may experience less shear thinning and exhibit a relative increase in shear viscosity). The resultant lower shear viscosity may cause the adhesive to build up on the applicator, for example at the edge of the applicator adjacent to the applicator outlet (e.g., nozzle tip or slot edge). As the adhesive builds up on the applicator, one or more adhesive blobs may fall off the applicator and onto the moving web, causing undesirable contamination of the substrate.

Accordingly, it would be desirable to provide an absorbent article constructed with a low basis weight substrate and a hot-melt adhesive that provides suitable adhesive bond strength and low bleed-through. It would also be desirable to provide an absorbent article constructed with a hot-melt adhesive that has a suitable shear viscosity through a desired range of process conditions. It would further be desirable to provide a process for constructing an absorbent article with a low application temperature adhesive.

SUMMARY OF THE INVENTION

In order to provide a solution to the problems described above, at least one embodiment herein provides a disposable absorbent article for receiving and storing bodily exudates. The disposable absorbent article comprises a topsheet, an outer cover and an absorbent core assembly disposed between the topsheet and outer cover. The disposable absorbent article also included a first substrate and a second substrate. At least one of the first and second substrates has a basis weight of less than 15 grams per square meter. At least a portion of the first substrate and the second substrate are adhesively bonded to one another with a low application temperature adhesive.

DETAILED DESCRIPTION OF THE INVENTION

Definitions

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings, such as the diaper illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Bleed-through" means the phenomenon related to applying hot melt or other adhesive to a porous material such as a nonwoven when the adhesive penetrates into the porous material far enough to reside sufficiently close to the opposite surface of the material to which it was applied ("non-applied side") such that it is capable of attaching (i.e., contaminating and/or adhering) to other materials or objects placed against the porous material on the non-applied side. The distance that an adhesive penetrates into a material may be determined by examining a cross section of the adhesive containing material and measuring the distance from the adhesive side of the material to the farthest point traveled by the adhesive through the thickness of the material.

"Disposable" means articles that are generally not intended to be laundered or otherwise restored or reused. (i.e., they are intended to be discarded after a single use and, preferably, to be recycled, composted or otherwise discarded in an environmentally compatible manner).

"Disposed" means the placement of one element of an article relative to another element of an article. For example, the elements may be formed (joined and positioned) in a particular place or position as a unitary structure with other elements of the diaper or as a separate element joined to another element of the diaper.

"Film" means a substantially nonporous, sheet-like material wherein the length and width of the material far exceed the thickness of the material. Typically, films have a thickness of about 0.5 mm or less. Films used in disposable absorbent articles may be configured to be liquid impermeable and/or vapor permeable (i.e., breathable).

"Joined" means configurations whereby an element is directly secured to another element by affixing the element directly to the other element and to configurations whereby an element is indirectly secured to another element by affixing the element to intermediate member(s), which in turn are affixed to the other element.

"Laminated structure" or "laminate" means a structure in which one layer, material, component, web, or substrate is joined, at least in part, to another layer, material, component, web, or substrate. As stated elsewhere in this application, a layer, material, component, web, or substrate may be folded over and adhesively bonded to itself to form a "laminated structure" or "laminate."

"Lateral" direction means the direction running from a longitudinal edge to an opposing longitudinal edge of the article and generally at a right angle to the longitudinal direction. Directions within 45 degrees of the lateral direction are considered to be "lateral."

"Longitudinal" direction means the direction running substantially perpendicular from a waist edge to an opposing waist edge of the article and generally parallel to the maximum linear dimension of the article. Directions within 45 degrees of the longitudinal direction are considered to be "longitudinal" "Low application temperature" ("LAT") hot-melt adhesives are hot-melt adhesives that are intended to be applied at a temperature of less than 150° C. Hot-melt adhesives are recognized in the art as adhesives that are substantially solid at room temperature (e.g., 21-25° C.) and upon the application of heat (e.g., higher than 90° C.) become substantially fluid for use in an adhesive application.

"Low basis weight substrate" means a substrate (e.g., nonwoven, film, or web) that has a basis weight of less than 15 grams per square meter ("gsm"), when measured according the Basis Weight Test described below.

"Nonwoven" means a manufactured sheet, web, or batt of directionally or randomly oriented fibers, bonded by friction, and/or cohesion, excluding paper and products which are woven, knitted, tufted, stitchbonded, incorporating binding yarns or filament, or felted by wet milling, whether or not additionally needled. The fibers may be of natural or man-made origin. The fibers may be staple or continuous filaments or be formed in situ. The porous, fibrous structure of a nonwoven may be configured to be liquid permeable or impermeable, as desired.

"Viscosity" is the measure of the internal friction of a fluid in motion, and is characterized as the ratio of shear stress to shear rate of a fluid. Viscosity may be expressed in units of Pascal-seconds ("Pa-s"). For a Newtonian fluid, viscosity is generally considered to be substantially constant at all shear rates. For a non-Newtonian fluid, viscosity is generally considered to vary with shear rate. "Apparent viscosity" is used to describe the Newtonian fluid behavior, while "shear viscosity" is used to describe non-Newtonian fluid behavior at a particular shear rate. Viscosity is conventionally reported in the adhesive literature as apparent viscosity measured, for example, with a Brookfield viscometer according to ASTM D3236-88.

"Web" means a material capable of being wound into a roll. Webs may be films, nonwovens, laminates, apertured laminates, etc. The face of a web refers to one of its large two dimensional surfaces, as opposed to its edge.

Hot-Melt Adhesive

Suitable base polymers for use in formulating hot-melt adhesives as disclosed herein include, without limitation, block or multi-block copolymers having the general configuration: A-B-A or A-B-A-B-A-B. The polymer blocks A may be non-rubbery polymer blocks, which have glass transition temperatures above 20° C. (as homopolymers). Suitable examples for polymer blocks A include, without limitation, homopolymers or copolymers of vinyl monomers such as vinyl arenes, vinyl pyridines, vinyl halides and vinyl carboxylates; homopolymers or copolymers of acrylic monomers such as acrylonitrile, methacrylonitrile, and esters of acrylic acids; monovinyl aromatic hydrocarbons of the benzene series such as styrene, vinyl toluene, vinyl xylene, ethyl vinyl benzene; dicyclic monovinyl compounds such as vinyl naphthalene and the like; polymer blocks derived from alpha olefins, alkylene oxides, acetals, and urethanes. The rubbery polymer blocks B may include butadiene, isoprene, propylene, butylene, and/or ethylene, which is partially or substantially hydrogenated. Common examples of rubbery block copolymers include, without limitation, polystyrene-polybutadiene-polystyrene ("SBS"), polystyrene-polyisoprene-polystyrene ("SIS") and polystyrene-poly-(ethylenebutylene)-polystyrene ("SEBS") and polystyrene-poly-(ethylenepropylene)-polystyrene ("SEPS"). These copolymers may be prepared using methods taught, for example, in U.S. Pat. Nos. 3,239,478; 3,427,269; 3,700,633; 3,753,936; and 3,932,327. Suitable rubbery block copolymers may also be obtained from Shell Chemical Co. under the trademarks KRATON 1101, 1102, 1107, 1650, 1652 and 1657; from Enichem under the tradename EUROPRENE; and from Firestone Tire and Rubber Company under the tradename STEREON 840A. Mixtures of copolymers such as blends of SBS and SIS may also be used. The block copolymer component of the adhesive will generally be present at a level of from 10 to 25% by weight of the adhesive composition.

Hot-melt adhesives for use herein may also include one or more waxes. Suitable waxes include petroleum derived wax and conventional wax. The term "petroleum derived wax" includes both paraffin and microcrystalline waxes having melting points of from 130° F. to 225° F. and synthetic waxes such as low molecular weight polyethylene or Fisher-Tropsch waxes. Commercially available examples of suitable microcrystalline waxes include, without limitation, MICROSERE 5999 (melting point of 90.5° C.) and MICROSERE 5812 (melting point of 85° C.) both available from IGI. Amounts of microcrystalline wax present in a hot-melt adhesive may range from 1 to 10 wt % by weight of the adhesive composition.

Tackifying resins useful in the disclosed hot-melt adhesive compositions include hydrocarbon resins, synthetic polyterpenes, rosin esters, natural terpenes, and the like. The tackifying agent may be present at a level of from 40 to 70% by weight of the adhesive composition, e.g., 60% by weight. More particularly, and depending upon the particular base polymer, the useful tackifying resins may include any compatible resins or mixtures thereof such as natural and modified rosins including, for example, as gum rosin, wood rosin, tall oil rosin, distilled rosin, hydrogenated rosin, dimerized rosin, and polymerized rosin; glycerol and pentaerythritol esters of natural and modified rosins, including, for example as the glycerol ester of pale wood rosin, the glycerol ester of hydrogenated rosin, the glycerol ester of polymerized rosin, the pentaerythritol ester of hydrogenated rosin, and the phenolic-modified pentaerythritol ester of rosin; copolymers and terpolymers of natural terpenes, including, for example, styrene/terpene and alpha methyl styrene/terpene; polyterpene resins having a Ring and Ball softening point, as determined by ASTM method E28-58T, of from about 80° C. to 150° C.; phenolic modified terpene resins and hydrogenated derivatives thereof including, for example, the resin product resulting from the condensation, in an acidic medium, of a bicyclic terpene and a phenol; aliphatic petroleum hydrocarbon resins having a Ball and Ring softening point of from about 70° C. to 135° C.; aromatic petroleum hydrocarbon resins and the hydrogenated derivatives thereof; and alicyclic petroleum hydrocarbon resins and the hydrogenated derivatives thereof. Mixtures of two or more of the above described tackifying resins may be used for some formulations. Also included are the cyclic or acyclic $C_5$ resins and aromatic modified acyclic or cyclic resins. It may be particularly desirable to use one or more natural rosin esters as the tackifier, due to their sustainability (i.e., replenished by nature).

One or more plasticizing or extending oils may be present in the hot-melt adhesive in amounts of from 15% to 30% (e.g., 21%, by weight of the adhesive). Suitable examples of plasticizing or extending oils include olefin oligomers and low molecular weight polymers, vegetable and animal oil, and their derivatives. The petroleum derived oils may be relatively high boiling materials containing only a minor proportion of aromatic hydrocarbons (e.g., less than 30% or even less than 15% by weight of the oil). It may be desirable to use oil that is entirely non-aromatic. Suitable oligomers include polypropylenes, polybutenes, hydrogenated polyisoprene, hydrogenated polybutadiene, or the like having average molecular weights between 350 and 10,000. Examples of oils suitable for use herein include LUMINOL T350, a mineral oil available from Petrocanada and KAYDOL OIL available from Witco Corporation. Naphthenic oils, such as Calsol 5550, available from Calumet may also be useful.

Additives such as antioxidants, stabilizers, and/or pigments may also be included in the disclosed hot-melt adhesive in amounts of up to 3% by weight (e.g., 0.5% by weight). Nonlimiting examples of additives include hindered phenols or hindered phenols in combination with a secondary antioxidant such as distearyl thiodipropionate ("DSTDP") or dilauryl thiodipropionate ("DLTDP"). Representative examples of hindered phenols include: 1,3,5-trimethyl 2,4,6-tris(3,5-di-tert-butyl-4-hydroxybenzyl)benzene; pentaerythrityl tetrakis-3(3,5-di-tert-butyl-4-hydroxyphenyl)propionate; pentaerythritol tetrakis(3-lauryl thiodipropionate); n-octadecyl-3,5-di-tert-butyl-4-hydroxyphenol)-propionate; 4,4'-methylenebis(2,6-tert-butylphenol); 4,4'-thiobis(6-tert-butyl-o-cresol); 2,6-di-tertbutylphenol; 6-(4-hydroxyphenoxy)-2,4-bis(n-octylthio)-1,3,5-triazine; di-n-octadecyl 3,5-di-tert-butyl-4-hydroxy-benzyl-phosphonate; 2-(n-octylthio)ethyl 3,5-di-tert-butyl-4-hydroxy-benzoate; and sorbitol hexa[3-(3,5-di-tert-butyl-4-hydroxyphenyl)-propionate]. Commercial examples include IRGAFOS 168, a secondary antioxidant available from Ciba and IRGANOX 1010, a hindered phenol primary antioxidant available from Ciba-Geigy. Other antioxidants include ETHANOX 330, a hindered phenol from Albermarle; SANTOVAR, a 2,5 ditert-amyl hydroquinone from Monsanto; and NAVAGARD P a tris(p-nonylphenyl)phosphite from Uniroyal. Other additives conventionally used in hot-melt adhesives to satisfy different properties and meet specific application requirements also may be included. Such additives include, for example, fillers, pigments, flow modifiers, dyestuffs, which may be incorporated in minor or larger amounts into the adhesive formulation, depending on the purpose.

Hot-melt adhesives suitable for use herein may be characterized by apparent viscosity or shear viscosity. Characterizing a hot-melt adhesive according to its shear viscosity may provide a good indication of whether a hot-melt adhesive is suitable for a particular process condition or range of conditions, because shear viscosity tends to characterize the behavior of a fluid at a relatively high shear rate or across a range of relatively high shear rates, which may be correlated to a particular manufacturing process and/or process step. In certain manufacturing processes such as, for example, disposable diaper manufacturing processes, a hot-melt adhesive may be subjected to shear rates of greater than 5,000 $sec^{-1}$, 10,000 $sec^{-1}$, 20,000 $sec^{-1}$, 50,000 $sec^{-1}$, 100,000 $sec^{-1}$, or even 200,000 $sec^{-1}$, depending on the process conditions desired at a particular time. In certain embodiments, a slot-coater type adhesive applicator may be used to apply adhesive to the surface of a substrate. The shear rate inside the applicator may vary from 5,000 to 50,000 $sec^{-1}$, but the shear rate at, for example, the outer edge of the applicator may be as high as 500,000 $sec^{-1}$. Apparent viscosity, on the other hand, may illustrate important distinctions between adhesives that are not apparent from the measurement of shear viscosity, because apparent viscosity tends to characterize the behavior of a fluid at relatively low shear rates (e.g., less than 10 $sec^{-1}$). For example, when a particular set of test conditions does not permit an accurate measurement of one or more of the adhesives being compared (e.g., when the adhesive temperature is too high or too low), then apparent viscosity may provide a way to distinguish the adhesives. Apparent viscosity is determined according to ASTM D3236-88 at a temperature of 120° C. or 150° C.

In some instances, a change in adhesive shear viscosity may be compensated for by changing the adhesive temperature. For example, if the shear viscosity of the adhesive becomes undesirably high due to a decrease in manufacturing line speed (and a corresponding decrease in application pressure and shear rate), then the temperature at which the adhesive is applied may be increased, for example, to 150° C. to offset the undesired viscosity change. However, adhesive application temperatures of less than 150° C. or even less than 130° C., for example between 120° C. and 130° C., may still be desired even when adjusting the shear viscosity of the hot-melt adhesive in order to avoid undesirable thermal damage to the substrate. LAT adhesives suitable for use herein may demonstrate desirable shear viscosities at both low temperature applications (e.g., less than 130° C.) and high temperature applications (e.g., greater than 130° C.). For example, LAT adhesives suitable for use herein may have a shear viscosity of between 1.5 and 4.0 Pa-s at a shear rate of 5,000 $sec^{-1}$; between 0.8 and 3.0 Pa-s at 20,000 $sec^{-1}$; and between 0.3 and 1.5 Pa-s at 50,000 $sec^{-1}$, when measured according to the Shear Viscosity Test described herein. In order to provide a flexible manufacturing process, it may be desirable to select LAT adhesives that exhibit the shear viscosities disclosed above at temperatures of between 90 and 180° C. (e.g., 150° C., 130° C., or even 120° C.). Suitable LAT adhesives herein may have a glass transition temperature ($T_g$) of between 9 and 22° C., when measured according to ASTM D7028-07e1, titled "Standard Test Method for Glass Transition Temperature (DMA Tg) of Polymer Matrix Composites by Dynamic Mechanical Analysis (DMA)." Suitable LAT adhesives herein may have a G' at 25° C. of between 30,000 and 50,000 (±20%); a G' at 37° C. of between 17,500 and 32,500 (±20%); and a G' at 100° C. of between 50 and 100 (±20%). One example of a suitable LAT adhesive for use herein is sold under the trade name NW1194 by the H.B Fuller Co., St. Paul, Minn. Another particularly suitable example of an LAT adhesive is sold under the trade name DN626C by Henkel (formerly National Starch and Chemical Co.) Bridgewater, N.J.

Figure 1A:
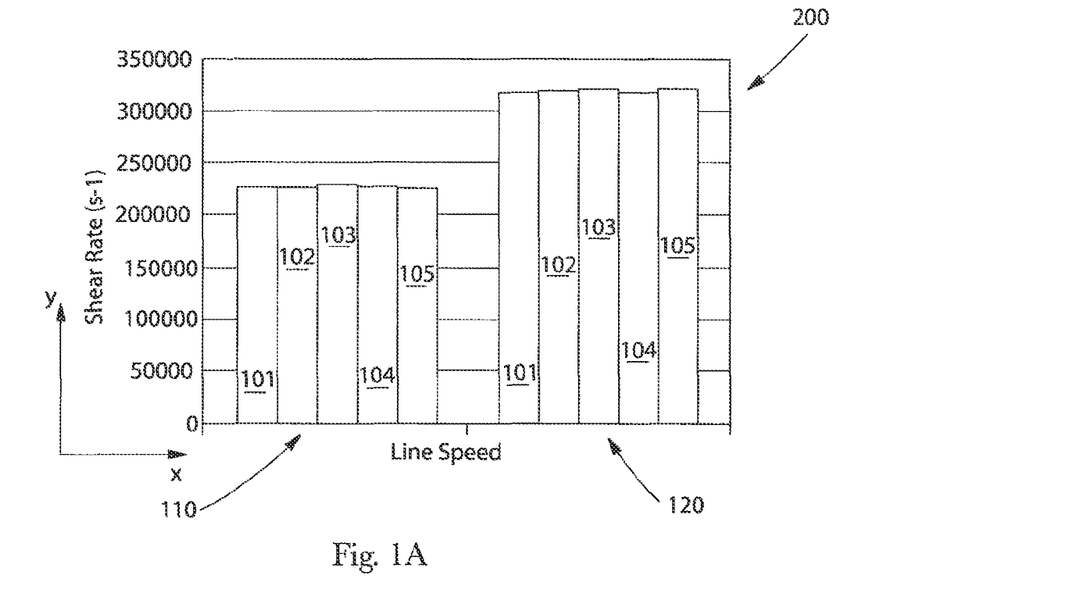
FIG. 1A is a bar chart comparing the shear rate versus line speed characteristics of hot-melt adhesives.

FIG. 1A shows a chart 200 illustrating the shear rates (y-axis) of five hot-melt adhesives 101, 102, 103, 104, and 105 at two line speeds (x-axis). The first line speed 110 is less than the second line speed 120. As shown in FIG. 1A, an increase in line speed is accompanied by a commensurate increase in shear rate, due at least in part to an increase in adhesive application pressure (i.e., applicator pressure is increased to maintain a constant adhesive flow rate on the faster moving line). The first adhesive 101 is a hot-melt adhesive sold under the product code HL-1358LO by the H.B Fuller Company, St. Paul, Minn. The first adhesive 101 comprises a styrenic block copolymer (styrene-isoprene-styrene ("SIS")), tackifyer, plasticizer, and additives. The second adhesive 102 is a hot-melt adhesive sold under the product code DM526 by National Starch and Chemical Corporation, New Jersey. The second adhesive 102 comprises a mix of styrenic block copolymers (SIS and styrene-butadiene-styrene ("SBS")), tackifyer, plasticizer, and additives. The third adhesive 103 is a hot-melt adhesive sold under the product code DN626C by the National Starch and Chemical Corporation, New Jersey. The third adhesive 103 comprises a mix of styrenic block copolymers (SIS and SBS)), tackifyer, plasticizer, and additives. The fourth adhesive 104 is a hot-melt adhesive sold under the product code D3166 by the H.B Fuller Company, St. Paul, Minn. The fourth adhesive 104 comprises a polyolefin polymer, a tackifyer, a plasticizer, and additives. The fifth adhesive 105 is a hot-melt adhesive sold under the product code NW 1194 by the H.B Fuller Company, St. Paul, Minn. The fifth adhesive 105 comprises a mix of styrenic block copolymers (e.g., SIS and SBS), a tackifyer, a plasticizer, and additives.

Figure 1B:
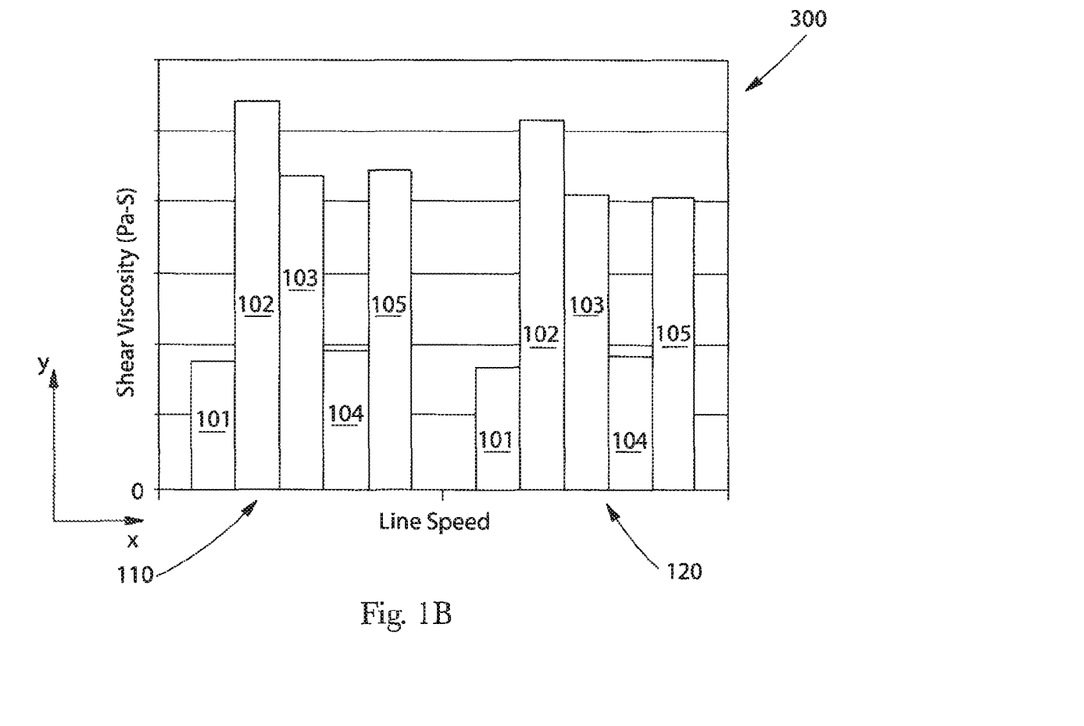
FIG. 1B is a bar chart comparing the shear viscosity versus line speed characteristics of hot-melt adhesives.

FIG. 1B shows a chart 300 illustrating the shear viscosity (y-axis) that the five hot-melt adhesives 101, 102, 103, 104, and 105 exhibit at the first and second line speeds 110 and 120. As can be seen in FIG. 1B, the shear viscosity may vary between different adhesives and different line speeds.

Disposable Absorbent Article

In certain embodiments, the disposable absorbent article may take the form of a wearable article intended to be worn about the lower torso of wearer (e.g., a diaper, pant, pant-like article, or incontinence article). Such articles may include a topsheet positioned in close proximity to or even touching the body of the wearer when the article is worn as intended; an outer cover (sometimes referred to as a backsheet in a traditional diaper) positioned in close proximity to or even touching the garment of a wearer when the article is worn as intended; and an absorbent core assembly positioned between the topsheet and the outer cover. The outer cover is typically included to prevent bodily exudates contained in the absorbent core assembly from escaping from the article, and in some instances to provide desirable tactile or other desirable material properties (e.g., softness, opacity, breathability). The outer cover may be configured to be liquid impermeable and/or vapor permeable (i.e., breathable). Generally, at least a portion of the topsheet is liquid permeable to permit liquid to readily pass through the thickness of the topsheet. The topsheet may be joined to one or more portions of the absorbent core assembly and/or outer cover. The outer cover may be joined to one or more portions of the absorbent core assembly and/or topsheet. One or both of the topsheet and outer cover may be configured as a laminate (i.e., include more than one layer of material). For example, the outer cover may include one or more layers of soft, nonwoven material (e.g., spunbond or meltblown polyethylene fibers) joined to one or more layers of liquid-impermeable, breathable film and/or nonwoven material. In certain embodiments, the topsheet and outer cover may be coextensive and joined to one another along their respective peripheries to surround and envelop the absorbent core assembly. Disposable absorbent articles disclosed herein may include one or more hot-melt adhesives and/or LAT adhesives. The adhesive is typically applied to a substrate while the adhesive is in a molten state and then contacted with a different substrate or another portion of the same substrate to form a laminate structure. The adhesive can be applied to one or more portions of one or more substrates such as a nonwoven or film web by any suitable method known in the art (e.g., coating or spraying) in an amount sufficient to enable a suitable adhesive bond to be formed between the substrates. The substrate may be a nonwoven, film, tissue, scrim, mesh, combinations of these and the like. Materials for use in a substrate may include any suitable natural or synthetic material known in the art (e.g., one or more polyolefins such as polypropylene and polyethylene; polyester; cellulose; rayon; cotton). The fibers in the nonwoven may be made by any suitable process known in the art (e.g., spunbonding, meltblowing, carding, airlaying, hydroentanglement) and have any suitable fiber size desired. Suitable fiber diameters include diameters of between 100 nm to 20 µm, for example, between 3 and 6 µm. Traditional nonwoven substrates typically have a basis weight of greater than 15 gsm, for example, between 15 and 25 gsm, however, it may be desirable to include one or more low basis weight substrates in a disposable absorbent article. For example, it may be desirable to include a low basis weight substrate in the topsheet, outer cover, leg cuff(s), ear(s), fastener, absorbent core assembly, and/or any other component of the absorbent article, as desired. Low basis weight substrates suitable for use herein include films and nonwovens having a basis weight of, for example, between 3 and 15 gsm; between 8 and 14 gsm; 12 gsm; or 13 gsm. One example of a low basis weight substrate is a low basis weight breathable film that includes 50% by weight polyethylene-based polyolefins and 50% by weight calcium carbonate filler particles, based on the weight of the substrate. In this example, the low basis weight breathable film may be extruded, cooled, and then permanently deformed by, e.g., stretching in one or more directions to create interconnecting micropores within the film structure. Another example is an 11 gsm spunbond nonwoven material suitable for use as a dusting layer, available from Pegas Nonwovens, Znojmo, Czech Republic. Another example is a 10 gsm spunbond nonwoven suitable for use as a core cover, available from Fibertex, Aalborg, Denmark. Suitable adhesive bonds formed between a low basis weight substrate and another article component or between a low basis weight substrate and itself have Peel Hang Time values of greater than 120 seconds, 200 seconds, 500 seconds, or even 1000 seconds when measured according to the Peel Hang Time Test. Materials having basis weights other than between 3 and 15 gsm may be suitable for use in disposable absorbent articles, but generally do not provide the cost savings and/or other benefits of the low basis weight materials disclosed herein.

A suitable absorbent core assembly for use with the absorbent articles disclosed herein may include a wide variety of liquid-absorbent materials commonly used in disposable diapers and other absorbent articles (e.g., cellulose fibers, superabsorbent polymers ("SAP"), and/or absorbent gelling materials ("AGM")). The core assembly may include one or more layers of liquid absorbing material. In certain embodiments, the absorbent core assembly may include multiple layers, where each layer is intended to serve a particular purpose. For example, one or more layers may be fluid handling layers (e.g., acquisition layers and/or distribution layers which are not intended to permanently store liquid), while one or more other layers are configured to be storage layers for the permanent storage of liquid. The absorbent core assembly may also include layers to stabilize other core components such as, for example, a core cover and/or dusting layer. Exemplary absorbent structures for use as an absorbent core assembly or portion(s) thereof are described in U.S. Pat. Nos. 4,610,678; 4,673,402; 4,834,735; 4,888,231; 5,137,537; 5,147,345; 5,342,338; 5,260,345; 5,387,207; 5,397,316; and 5,625,222 and in U.S. Publication Nos. 2004/0162536 and 2004/0167486. It should also be recognized that other structures, elements, or substrates may be positioned in a joined or unjoined relationship between the core, the topsheet and/or the outer cover. Nonlimiting examples of suitable disposable absorbent article configurations are described generally in U.S. Pat. Nos. 3,860,003; 4,808,178; 4,909,803; 5,151,092; 5,221,274; 5,554,145; 5,569,234; 5,580,411; and 6,004,306.

It is known that on occasion swollen or partially swollen SAP particles disposed in the absorbent core assembly of an absorbent article may escape from the core and/or article and contaminate the skin of a wearer. This phenomenon, which is sometimes referred to as a gel on skin occurrence, is generally considered to be undesirable by consumers. Therefore, in certain embodiments, an absorbent article may include one or more end-flap seal, end seals, and/or side seals to prevent or at least reduce the possibility of SAP particles and/or other absorbent materials from escaping from the disposable absorbent article and/or absorbent core assembly. In certain embodiments, an end-flap seal may be formed by joining the topsheet to the backsheet along one or both longitudinal ends of the article with an LAT adhesive. The topsheet and backsheet may joined to one another by applying a suitable LAT adhesive to the backsheet and/or the topsheet (e.g., in a spiral pattern or slot coating with a comb-shim pattern) in the vicinity of their respective longitudinal ends, and then overlaying the topsheet onto the backsheet (or vice versa) during the open time of the adhesive such that the longitudinal ends of the topsheet and backsheet are substantially coterminous and adhesively bonded together. In certain embodiments, an end seal may be formed by joining the core wrap substrate and the dusting layer substrate to one another along the longitudinal end edge of the core assembly, for example, with a hot-melt adhesive. A side seal may be formed by joining the core wrap substrate and dusting layer substrate to one another along the longitudinal side edge of the core assembly in substantially the same way as the end seal. Suitable amounts of adhesive for forming an end-flap seal include amounts of between 2.5 and 5.0 grams of adhesive per square meter of substrate. Suitable examples of end seals and side seals may be found in U.S. Publication Nos. 2006/0155254 and 2006/0155253; and U.S. Pat. No. 7,013,941.

Figure 2:
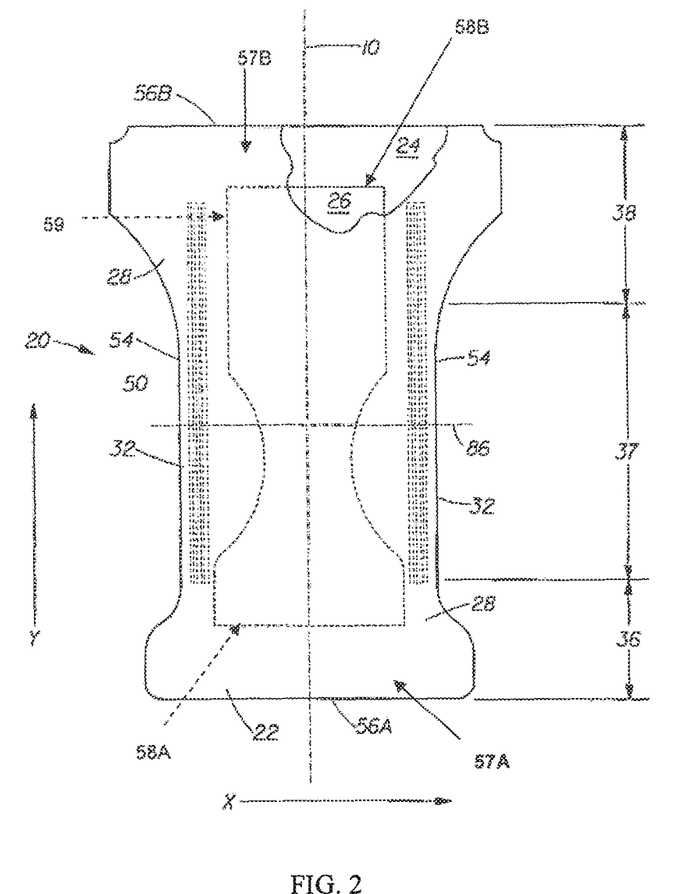
FIG. 2 is a partial cut away, plan view of a disposable absorbent article.

FIG. 2 shows an exemplary embodiment of a diaper 20. The diaper 20 shown in FIG. 2 is in a flat-out, uncontracted state (e.g., with no elastic induced contraction). The diaper 20 may include a liquid pervious topsheet 22; an outer cover 24 (which may act as a traditional, liquid impervious, optionally breathable diaper backsheet) joined with the topsheet 22; an absorbent core 26 positioned between the topsheet 22 and the outer cover 24; side panels 28; and leg cuffs 32. The diaper 20 may further include an outer, garment-facing surface opposed to an inner, wearer-facing surface 50, a first waist region 36, a second waist region 38 opposed to the first waist region 36, and a crotch region 37 positioned between the first and second waist regions 36 and 38. The diaper 20 may also include longitudinal edges 54, a first end edge 56A corresponding to the first waist region 36, and an opposing second end edge 56B corresponding to the second waist region 38. The diaper has a longitudinal centerline, which is substantially parallel to the linear regions of the longitudinal edges 54, and a lateral centerline 86, which is substantially parallel to the linear regions of the opposing end edges 56A and 56B. The diaper 20 may include first and second end-flap seals 57A and 57B formed, for example, by joining portions of the topsheet 22 and outer cover 24 to one another in the first and second waist regions 36 and 38 (e.g., adjacent the end edges 56A and 56B). The diaper may also include first and second end seals 58A and 58B positioned proximate to the end edges of the absorbent core 26. The end seals 58A and 58B may be formed by joining, for example, portions of a core over layer and dusting layer to one another in the vicinity of the core end edges. The diaper 20 may include a side seal 59 along all or a portion of one or both of the longitudinal side edges of the absorbent core 26. The side seal 59 may be formed by joining, for example, portions of the core cover layer and dusting layer to one another in the vicinity of the longitudinal side edges of the absorbent core 26.

Process for Making an Absorbent Article

An absorbent article may be formed by joining a first substrate and a second substrate in a face-to-face relationship to form a laminate structure, and incorporating the laminate into an absorbent article (i.e., the laminate is joined to itself and/or other components to form the absorbent article). The first and second substrates may be joined to one another with a hot-melt adhesive (e.g., an LAT hot-melt adhesive) applied to one or both substrates. The first and/or second substrate may be a low basis weight film or nonwoven web (e.g., a 13 gsm polyethylene film). In certain embodiments, the first and/or second substrate may include two or more layers of film and/or nonwoven material. The individual layers of the first and/or second substrate may be joined together by any suitable means known in the art (e.g., adhesive and/or high pressure bonding). The first and/or second substrates, and/or layers thereof, may be fed into the absorbent article manufacturing process from a roll of feedstock, as is known in the art. In certain embodiments, the first and/or second substrates, and/or layers thereof, may be formed in an upstream process and fed directly into the absorbent article manufacturing process. It is to be understood that any suitable means for inputting a web of material into a manufacturing process is contemplated herein. The rate at which the first and/or second substrate is fed into the process may vary with the speed of the manufacturing line speed.

One or more LAT adhesives may be applied to one or more portions of the first and/or second substrate and/or layers thereof. The LAT adhesive(s) may be applied to the first and/or second substrate in any amount and/or rate desired, as long as suitable bond strength, bleed-through, and contamination properties are obtained. In certain embodiments, the LAT adhesive may be applied to the substrate via one or more slot applicators (e.g., a SPEED-COAT brand slot applicator or an EP-11 brand slot applicator, both available from the Nordson Corporation, Westlake, Ohio) in order to substantially cover the entire target surface or surface portion of the substrate with adhesive. The slot applicator may be configured to apply an intermittent or continuous bead (where a bead is a substantially unbroken line) of LAT adhesive from between 10 mm and 200 mm wide (i.e., shortest dimension in the x-y plane of the substrate) at a rate of between 1 and 40 gsm. The slot applicator may include a comb shim to apply the adhesive in the form of two or more discrete beads. The shim may have tines configured to apply beads of adhesive that are 1 mm wide and 1 mm apart. In certain embodiments, the LAT adhesive may be applied with one or more nozzles (e.g., air-jet-type nozzles or extrusion-type nozzles). The nozzles may be separated by a center-to-center distance of between 20 and 30 mm and may be configured to apply one or more intermittent or continuous adhesive strands in a linear or spiral pattern at a rate of up to 100 milligrams per minute per nozzle or between 25 and 100 milligrams per meter per strand of adhesive. Each strand may have a width of between 1 and 20 mm as measured on the substrate. In certain embodiments, the LAT adhesive may provide an adhesive bond between the first and second substrates that has a peel hang time of greater than 120, 200, 400, 600 or even 1000 seconds, when measured according to the Peel hang Time Test. It may be desirable to select an LAT adhesive that has a suitable shear viscosity to at least reduce the potential for adhesive blob formation at the outlet of the applicator. When the applicator pressure and/or shear force increases, the adhesive may become less viscous and have an increased tendency to flow along the edges of the applicator, especially the tip or outermost edge of the applicator. As the adhesive collects on the applicator outlet, it may eventually become massive enough to overcome the capillary pressure holding it to the applicator surface. When this happens, the adhesive blob may fall onto the substrate causing undesirable thermal damage to the substrate, bleed-through, low bond strength, and/or contamination. Examples of undesirable contamination resulting from an adhesive blob falling onto the web include aesthetic defects and/or transfer of the adhesive to an undesirable location such as, for example, other absorbent article elements, processing equipment, skin, clothes, and/or packaging. Suitable LAT adhesives for use herein produce little or no contamination, as demonstrated by the lack of undesirable adhesive blobs dropping onto the substrate (i.e., zero adhesive blobs drop onto the substrate during a continuous five-minute run of the manufacturing line).

Figure 3A:
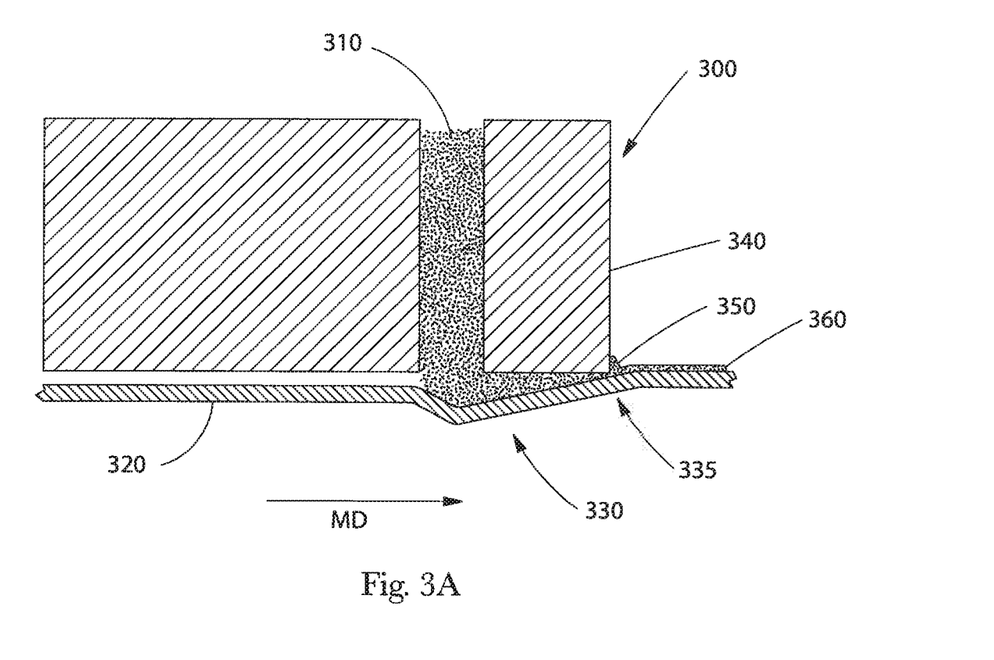
FIG. 3A illustrates a hot-melt adhesive application process.
Figure 3B:
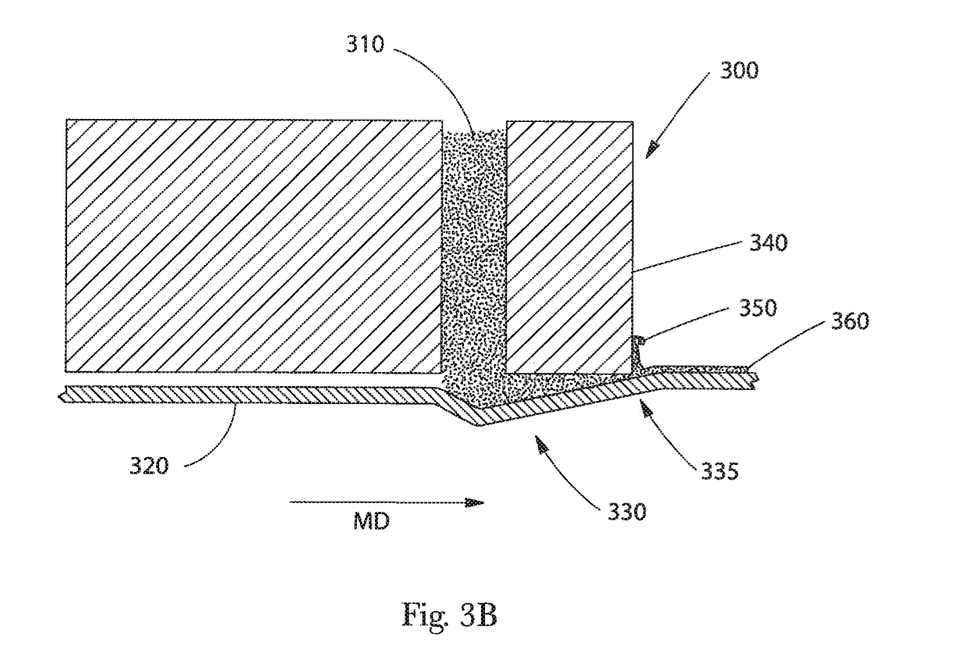
FIG. 3B illustrates a hot-melt adhesive application process.
Figure 3C:
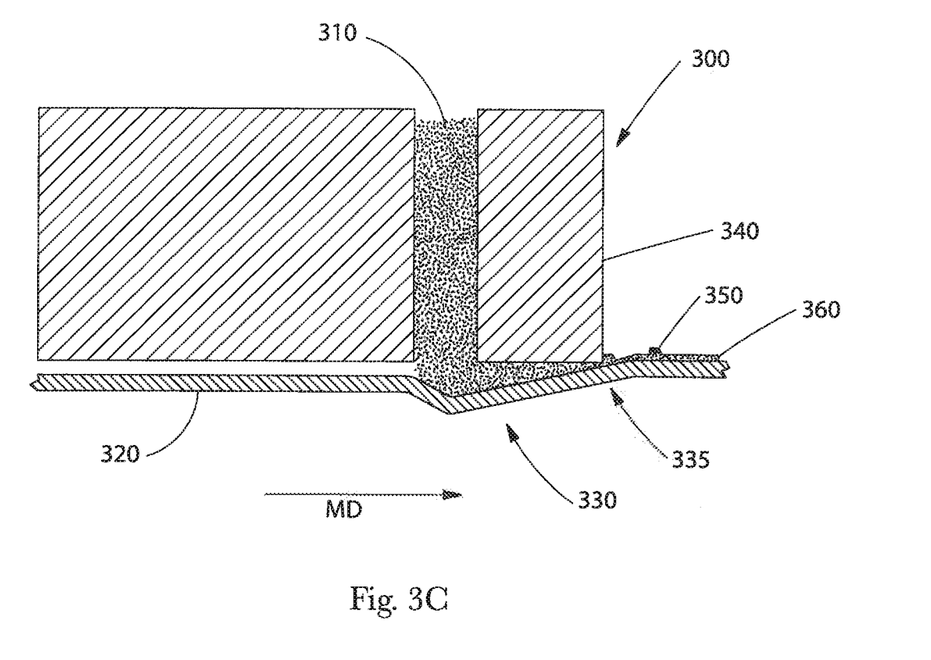
FIG. 3C illustrates a hot-melt adhesive application process.

FIGS. 3A-3C illustrate the formation of an adhesive blob 350 on a slot-coater type adhesive applicator 300 and the subsequent contamination of a moving web 320 by the adhesive blob 350. FIG. 3A shows a slot-coater type adhesive applicator 300 positioned above a moving web 320. The web 320 is moving in the machine direction MD. The adhesive applicator 300 passes adhesive 310 through a slot onto the surface of the web 320 at point 330. In certain configurations, the outer edge 340 of the adhesive applicator 300 may act as a sort of doctor blade, which provides a relatively consistent (e.g., in width, thickness, and/or basis weight) adhesive coating 360 on the surface of the web 320. The distance between the surface of the web 320 and the portion of the outer edge 340 closest to the surface of the web 320 determines the amount of adhesive 310 that remains on the surface of the web 320 as an adhesive coating 360. In certain embodiments, it may be desirable to provide a relatively thin adhesive coating 360 on the web 320, and therefore the volume of adhesive 310 that passes the outer edge 340 of the applicator 300 at point 335 may be relatively small compared volume of adhesive contacting the web at point 330. In certain embodiments, the shear force exerted on the adhesive 310 at point 335 may be high enough to impact the shear viscosity of the adhesive 310. If the shear viscosity of the adhesive 310 becomes low enough, an adhesive blob 350 may begin to form adjacent to the outer edge 340 of the applicator 300 at point 335. FIG. 3B illustrates a larger adhesive blob 350 that has grown over time. Eventually, the adhesive blob 350 may become large enough to fall onto the moving web 320, as shown in FIG. 3C. Absent a change in the process conditions or some other corrective action, adhesive blobs 350 may repeatedly build up on the outer edge 340 of the applicator 300 and fall onto the surface of the web 320, potentially causing structural and/or aesthetic defects to the web 320 and/or the articles into which the web 320 or portions of the web 320 are incorporated.

Figure 4:
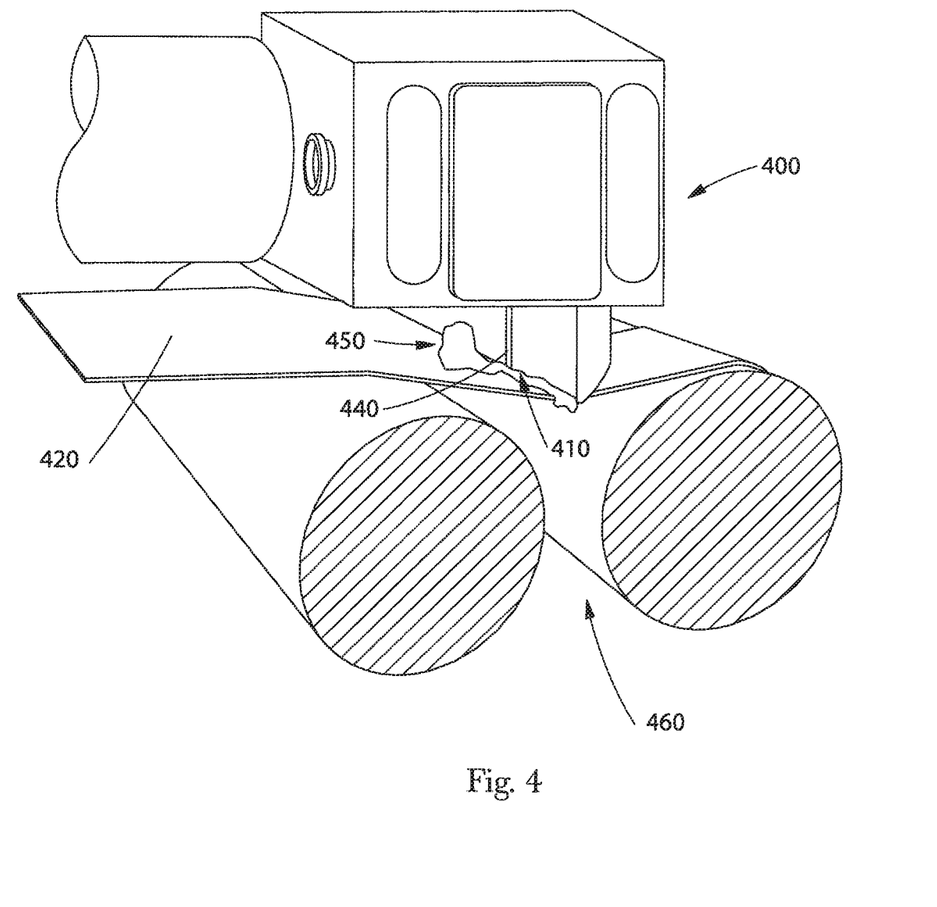
FIG. 4 is a representation of adhesive blob formation on an adhesive applicator.

FIG. 4 is a representation of a picture of a manufacturing line 460 that includes a slot-type adhesive applicator 400 applying a traditional hot-melt adhesive 410 to the surface of a substrate 420. As shown in FIG. 4, an adhesive blob 450 can be seen forming on the downstream edge 440 of the adhesive applicator 400.

Test Methods

Basis Weight Test

The Basis Weight Test determines mass per unit area of sheeted (planar) raw materials (except Pulp) by weighing a known area of sample. This test is carried out at a room temperature of 23° C. (±2° C.) and a relative humidity of 50% (±2%). The Basis Weight Test is based on ASTM D 756.

Equipment:
Hydraulic press/cutter capable of pressing steel cutting dies through paper and plastic samples such as the Alfa Cutter available from Thwing-Albert Frank GmbH Germany.
Balance with 0.001 g sensitivity, readable, calibrated and accurate to within 0.25% of the applied load.

Sample Preparation
1. Prior to testing bring the test samples to equilibrium for at least 2 hours at 23° C. (±2° C.) and 50% (±2%) relative humidity.
2. Count the required quantity of layers of the material (10 for thin samples, 1 for thick samples), lay them flat without folding and stamp out plies.
3. Sample Layers should be selected to be representative of the whole sample.

Test Procedure

Thin Materials (i.e., materials thinner than 1 mm):
1. Using the Press, Alfa Cutter or Equivalent Punch and a 100 cm$^2$ die, cut one pad (10 plies) without folding from the original sample. Each ply must be an individual layer from the tested material.
2. Weigh the cut sample (100 cm$^2$, 10 plies) on an analytical balance to the nearest 0.001 g and record the weight.

Thick Materials (i.e., materials 1 mm or thicker):
1. Using the Press, Alfa Cutter or Equivalent Punch and a 100 cm$^2$ die, cut one ply from the original sample.
2. Weigh the cut sample (100 cm$^2$, 1 ply) on an analytical balance to the nearest 0.001 g and record the weight.

Calculation(s)/Reporting

Thin Materials

Weight of 10 (100 cm$^2$ plies)*10=g/m$^2$.
Calculate and report data to the nearest 0.01 g/m$^2$.

Thick Materials

Weight of 10 single plies (100 cm$^2$ ply)*100=g/m$^2$

Shear Viscosity Test

Preparation of the Adhesive
If working with adhesive that comes in blocks, prepare as indicated below. If working with polymer in pellets, no preparation is needed.
1) Cut glue into chunks with a hot knife (melts through glue)
2) Put the chunks in between 2 sheets of release paper
3) Put the chunks into the freezer for up to 1 day
4) Cut the chunks with scissors into smaller pieces, approx 5 mm×5 mm Equipment
1) Use a capillary rheometer, e.g., Model No. D6052M-115, available from Dynisco Instruments, Franklin, Mass.
2) Select die #Z197-30; 0.5 mm diameter hole, 15.0 mm die length; Dynisco RMA #1129)
3) Make sure chamber and die are clean. If chamber is not clean, clean with cotton and mineral oil
4) Add some adhesive to the capillary chamber; push the adhesive out after molten.
5) Put die in screw with screw upside down
6) Put screw in bottom of rheometer chamber upside down
7) Tighten screw Procedure
1) Turn on rheometer
  a) Set the temperature to the temperature at which the shear viscosity of the adhesive sample is to be determined (e.g., 120° C., 130° C., or 150° C.);
  b) Set the 0.5 mm die diameter and the desired shear rate (i.e., 50,000 sec$^{-1}$ for the first run; 25,000, 10,000, and 5,000 sec$^{-1}$) the computer will indicate the correct ram rate;
  c) Delete all but the number of data points you want to collect
    i) Input ram rates as indicated by the computer (515 mm/min, etc.)
    ii) Select the "generate" option and the computer will fill in the shear rates
    iii) Set start position to 100 mm
    iv) Set point delay to 0 seconds
2) Ensure the machine is heating up properly;
3) Put glue pieces in the cylinder and pack the pieces firmly in with a hand-held ram until the cylinder is full;
4) Once the cylinder is full and the machine is at the desired temperature, allow the glue to soak in the cylinder for at least 10 minutes;
5) Position the ram-rod in the machine and secure in place according to the manufacturer's instructions;
6) Ensure the ram is properly lined up with the chamber as it goes in, so it does not bend;
7) Run the test.

Save Data to Generate a Graph of Viscosity Vs. Shear Rate:
1) Click PLOT on the screen that comes up. It plots Shear Viscosity vs. Residence Time in minutes;
2) Click the "Plot Table" button to sort out the data automatically;
3) Go to Edit→"Copy plot table to clipboard";
4) Open a spreadsheet and paste the data into the spreadsheet (e.g., EXCEL, available from the Microsoft Corporation, WA);
5) Paste all your data into the same spreadsheet file if you label for each run;
6) At end of your session, save your file onto your portable drive.

Peel Hang Time Test

The Peel Hang Time Test method is used to determine adhesive bond strength.

Equipment:
Scissors
Hunter Force gauge (e.g., Model 10 Bank Shear RT-10, available from ChemInstruments, Ohio).
Timer
Metal Ruler traceable to NIST, DIN, JIS or other comparable National Standard, graduated in mm, longer than the length to be measured.
300 g weight with clamp (300 grams is total weight. The width of the clamp is between 1-1.5× the width of the sample, and the clamping force is such that the clamp does not slip when hanging freely from the sample).

Procedure: the procedure below is exemplified for the end flap seal of a disposable diaper, but it is believed that one of ordinary skill in the art could readily adapt this procedure to measure the bond strength of an adhesive bond between any multi-layer nonwoven and/or film laminate.

Figure 5:
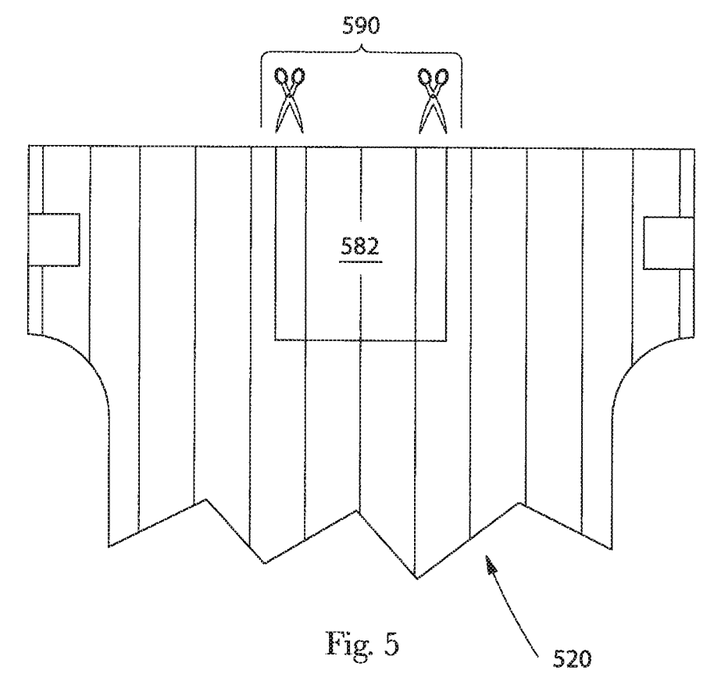
FIG. 5 is a partial plan view of a disposable absorbent article.
Figure 6:
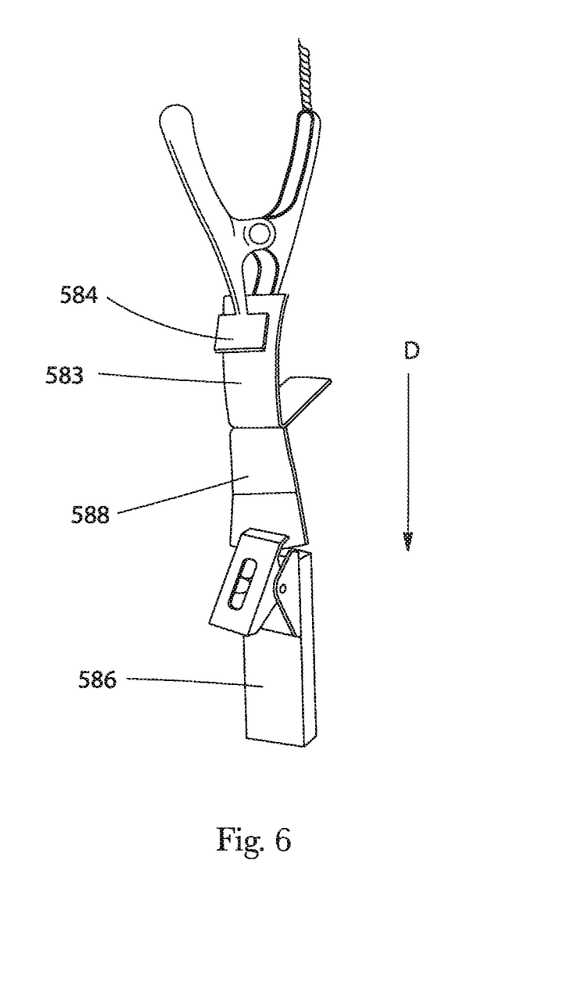
FIG. 6 is a cross-section view of the Peel Hang Time Test setup.

FIGS. 5 and 6 are provided to illustrate particular portions of the Peel Hang Time Test. Environmental conditions for this test are 23° C.±2° C. and 50%±2% relative humidity. Equilibrate samples at the environmental conditions for one hour prior to testing. If the sample to be tested is taken from the end flap seal of a disposable diaper 520 and the diaper 520 is in a folded configuration (i.e., bifolded or trifolded), open up the diaper 520 so that it is in a flat-out configuration. Determine if one end flap seal of the diaper 520 is shorter than the other in the MD. From the shorter end flap seal of the diaper 520 cut out a 40 mm wide (CD)×50 mm long (MD) test strip 582 from the center 590 of the diaper 520, as shown in FIG. 5. If both end flap seals are the same length, select one and cut out a test strip as described above. Fold out the test strip 582 like a book by separating two of adjacent unbonded ends of the substrate layers (i.e., the ends that were positioned closest to the absorbent core assembly). Carefully remove any core material that may be present. If the test strip 582 includes only two substrates (i.e., is a two-layer laminate), clamp the end of the first substrate 583 making up the test strip 582 into the jaw 584 of the Hunter gauge as shown in FIG. 6. Attach the weight 586 to the end of the second substrate (as shown in FIG. 6) and lower slowly until the weight hangs freely on the test strip 582 in the downward direction D. Samples taken from articles other than disposable diapers and/or components that do not form an end flap seal should be sized as indicated in this method (i.e., 45 mm wide by 60 mm long). The sample is taken such that the width (i.e., the 45 mm dimension) includes an adhesive bond substantially from edge to edge in the width dimension (however, it is to be understood that the bond need not necessarily be continuous across the entire width), and the sample is positioned in the Hunter gauge grip such that width is perpendicular to the downward direction D. If the test strip 582 includes more than two layers (i.e., is a three or more layer laminate) select two layers that are adjacent to one another and prepare them as indicated above. Start the timer as soon as the weight 586 hangs freely in the downward direction D. Stop the timer immediately after the weight 586 has fallen off. Report the determined value(s) to the nearest 1 second. Repeat the test on 10 samples and record the individual hang times. Average the individual hang times and report the average value as the peel hang time.

Examples

Table 1 below lists six hot melt adhesives and a variety of properties for each adhesive. The first five adhesives are the same as the adhesives 101-105 described in FIG. 1. The last adhesive is a hot-melt adhesive sold under the trade name DM426N, and is available from the National Starch and Chemical Company. DM426N includes a styrenic block copolymer (SBS), tackifyer, plasticizer, and additives. Table 1 illustrates the apparent and shear viscosities of hot-melt adhesives at 120° C. and 150° C. The apparent viscosities are measured according to ASTM D3236-88, and the shear viscosities are measured according to the Shear Viscosity Test. Empty cells indicate test conditions for which data is unavailable (e.g., due to equipment limitations). Table 1 also shows peel hang time values in seconds. The peel hang times for each adhesive are measured according the Peel Hang Time method. The samples used for determining peel hang time are removed from a diaper as described in the Peel Hang Time method. The diapers are made on a commercial diaper production line. Table 1 also illustrates contamination as it is observed on the manufacturing line. As can be seen from Table 1, not all hot-melt adhesive provide suitable bond strength (as demonstrated by peel hang time) and flexible processing characteristics (as demonstrated by a suitable shear viscosity and no contamination).

TABLE 1

| Adhesive | Apparent Viscosity (Pa-s) at 120 C. | Apparent Viscosity (Pa-s) at 150 C. | Shear viscosity (Pa-s) at 120 C. | | | | Shear viscosity (Pa-s) at 150 C. | | | | Peel Hang Time (Sec) | Line Contamination for Slot coater |
|---|---|---|---|---|---|---|---|---|---|---|---|---|
| | | | 5,000 | 20,000 | 50,000 | 100,000 | 5,000 | 20,000 | 50,000 | 100,000 | | |
| HL-1358LO | >9.0 | 3.12 | — | — | — | — | 1.603 | 0.812 | 0.554 | 0.28 | 340 | no |
| DM526 | 18.22 | 4.3 | — | — | — | — | 4.0 | 1.93 | 1.228 | 0.4 | 520 | no |
| DN626C | 2.3 | 0.685 | 1.9 | 1.231 | 0.873 | 0.38 | — | — | — | — | 300-360 | no |
| D3166 | >14.0 | 4.792 | — | — | — | — | 2.1 | 1.033 | 0.667 | 0.3 | 118 | no |
| NW 1194 | 4.875 | 1.13 | 3.6 | 2.147 | 1.508 | 0.45 | — | — | — | — | 330 | no |
| DM426N | 24.9 | 3.5 | — | — | — | — | 3.3 | 1.689 | 1.37 | 0.68 | 78 | yes |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article for receiving and storing bodily exudates, the disposable absorbent article comprising:
    a topsheet, an outer cover and an absorbent core assembly disposed therebetween;
    a first substrate;

and a second substrate;
wherein at least one of the outer cover and topsheet comprise at least one of the first and second substrate and at least one of the first and second substrates is a nonwoven that has a basis weight of between 8 and 14 grams per square meter, and wherein the first substrate and the second substrate are adhesively bonded to one another with a low application temperature adhesive.

2. The disposable absorbent article of claim 1, wherein the first and second substrates exhibit no thermal damage as a result of being bonded to one another with the low application temperature adhesive.

3. The disposable absorbent article of claim 1, wherein the adhesively bonded first and second substrates have a peel hang time of greater than 120 seconds when measured according to the Peel Hang Time Test.

4. The disposable absorbent article of claim 1, wherein the adhesive has an apparent viscosity of less than 9 Pa-s at 120° C.

5. The disposable absorbent article of claim 1, wherein the adhesive has an apparent viscosity of less than 3 Pa-s at 150° C.

6. The disposable absorbent article of claim 1, wherein at least one of the first and second substrates is a film.

7. The disposable absorbent article of claim 1, wherein the adhesive has shear viscosity of between 0.8 and 3 Pa-s at a temperature of 120° C. and a shear rate of 20,000 $\sec^{-1}$.

8. The disposable absorbent article of claim 1, wherein the adhesive does not contaminate the first or second substrate with adhesive blobs at a temperature of between 120° C. and 130° C. and a shear rate of between 50,000 and 500,000 $\sec^{-1}$.

9. The disposable absorbent article of claim 1, wherein the adhesive includes at least 40% by weight based on the weight of the adhesive of a natural tackifying resin.

10. The disposable absorbent article of claim 9, wherein the natural tackifying resin is a rosin ester.

11. The disposable absorbent article of claim 1, wherein the adhesive penetrates the substrate to a depth of no more than 120 microns.

12. The disposable absorbent article of claim 1, wherein the adhesive is selected from the group consisting of SBS polymer, SIS polymer, and combinations of these.

13. The disposable absorbent article of claim 1, further comprising a core cover and a dusting layer, the core cover and the dusting layer being configured to envelop the absorbent core assembly, at least a portion of the core cover and the dusting layer being adhesively bonded to one another such that the adhesively bonded portion has a peel hang time of greater than 120 seconds according to the Peel Hang Time Test.

14. A disposable absorbent article for receiving and storing bodily exudates, the disposable absorbent article comprising:
  a. a topsheet comprising a first substrate, the first substrate comprising a nonwoven;
  b. an outer cover comprising a second substrate, the second substrate comprising a film;
  c. an absorbent core assembly disposed between the topsheet and outer cover; and
  d. first and second opposing longitudinal end edges,
  wherein at least one of the first and second substrates comprises a nonwoven that has a basis weight of between 8 and 14 grams per square meter and wherein at least a portion of the first substrate and the second substrate are adhesively bonded to one another with a low application temperature adhesive to form an endflap seal proximate to at least one of the first and second longitudinal end edges.

15. The disposable absorbent article of claim 14, wherein the first and second substrates exhibit no thermal damage as a result of being bonded to one another with the low application temperature adhesive.

16. The disposable absorbent article of claim 14, wherein the adhesively bonded first and second substrates have a peel hang time of greater than 120 seconds when measured according to the Peel Hang Time Test.

17. The disposable absorbent article of claim 14, wherein the adhesive has shear viscosity of between 0.8 and 3.0 Pa-s at a temperature of 120° C. and a shear rate of 20,000 $\sec^{-1}$.

18. The disposable absorbent article of claim 14, wherein the adhesive has an apparent viscosity of less than 9 Pa-s at 120° C.

19. The disposable absorbent article of claim 14, wherein the adhesive has shear viscosity of between 0.8 and 3.0 Pa-s at a temperature of 120° C. and a shear rate of 20,000 $\sec^{-1}$.

* * * * *